United States Patent [19]

Jones

[11] 4,098,713
[45] Jul. 4, 1978

[54] DETERGENT COMPOSITIONS

[75] Inventor: Kenneth L. Jones, Cincinnati, Ohio

[73] Assignee: The Procter & Gamble Company, Cincinnati, Ohio

[21] Appl. No.: 735,647

[22] Filed: Oct. 26, 1976

Related U.S. Application Data

[62] Division of Ser. No. 644,271, Dec. 24, 1975, abandoned.

[51] Int. Cl.² .................. C11D 1/02; C11D 1/66
[52] U.S. Cl. .................. 252/89; 252/DIG. 1; 252/DIG. 4; 252/117; 252/522; 260/615 R
[58] Field of Search .......... 252/89, DIG. 1, DIG. 14, 252/822, 161, 117; 260/615 R, 615 B

[56] References Cited

U.S. PATENT DOCUMENTS

| | | | |
|---|---|---|---|
| 3,102,893 | 9/1963 | Gaertner | 282/89 |
| 3,427,248 | 2/1969 | Lambert et al. | 252/117 |

FOREIGN PATENT DOCUMENTS 39-9878  8/1968  Japan.

*Primary Examiner*—Mayer Weinblatt
*Attorney, Agent, or Firm*—Steven J. Goldstein; Robert B. Aylor; Thomas H. O'Flaherty

[57] ABSTRACT

Compounds of the general formula

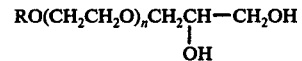

wherein R is an alkyl or alkenyl group of from 8 to 16 carbon atoms or an alkaryl group having an alkyl chain of from 5 to 13 carbon atoms and $n$ is a number from 1 to 6, are surfactant compounds having especial utility as grease and oil removing surfactants. The compounds can be utilized in built or unbuilt detergent compositions, either as the sole surfactant or as one component of a surfactant mixture.

8 Claims, No Drawings

DETERGENT COMPOSITIONS

This is a division of application Ser. No. 644,271, filed Dec. 24, 1975, now abandoned.

BACKGROUND OF THE INVENTION

This invention relates to detergent compounds and compositions and, in particular, to nonionic surfactants which are glyceryl ethers of ethoxylated compounds.

Conventional detergent compositions perform well in most situations but they do tend to be less effective in the removal of greasy and oily materials from fabrics than the consumer desires. This problem is particularly pronounced with certain of the newer synthetic fabrics and is also especially serious in the case of hydrocarbon-based oils such as used motor oil. There is therefore a need to provide surfactants which offer particular benefit in the area of grease and oil removal and which can form the basis of detergent compositions having improved performance in this area.

It has already been recognized that nonionic surfactants can offer some improvements in this area, and the incorporation of surfactants such as ethoxylated alcohols into detergent compositions does provide some benefit in oily stain removal. Unfortunately, this benefit does not extend equally to a wide spectrum of fabric/oily stain combinations and, in particular, even the best of the currently known oil-removing surfactants shows poorer performance on fabrics stained with used motor oil and relatively poorer performance on the removal of hydrocarbon oil stains on cotton when compared with triglyceride stains on cotton.

It is an object of the present invention to provide a surfactant compound which is particularly effective at removing oily stains, especially stains comprising hydrocarbon oil.

It is a further object of the present invention to provide detergent compositions incorporating the above mentioned surfactant material.

DETAILED DESCRIPTION OF THE PRIOR ART

Glyceryl ethers of unethoxylated alcohols are known materials and various uses have been suggested for them. For example, they have been suggested as fixing agents for perfumes in U.S. Pat. No. 2,091,162; as superfatting agents in soap in U.S. Pat. No. 2,157,022; and as extracting agents for organic substances in U.S. Pat. No. 2,156,724.

Furthermore, these and related materials having a glyceryl moiety have been suggested for use in detergent compositions for certain purposes. U.S. Pat. No. 2,768,956, issued Oct. 30, 1956 and assigned to Lever Brothers Company, discloses acylaryl glyceryl ethers in detergent compositions containing ionic non-soap surfactants. The glyceryl ethers in this case are said to be suds stabilizers. U.S. Pat. No. 2,900,346, issued Aug. 18, 1959 and assigned to Shell Development Company, also discloses the utility of glyceryl ethers as foam stabilizers for ionic, particularly sulfate and sulfonate, surfactants. U.S. Pat. No. 3,427,248, issued Feb. 11, 1969 and assigned to Lever Brothers Company, discloses the use of certain higher alkyl polyol ethers in combination with detergents as suds boosters and lime scum dispersants.

The utilization of naturally-occurring glyceryl ethers such as selachyl alcohol and batyl alcohol is discussed by M. Sulzbacher in Manufacturing Chemist, 1962, 33, 232, and it is suggested that these materials could have surface activity and could be made water-compatible by ethoxylation of the hydroxyl groups.

None of the above-disclosed glyceryl-containing materials can be considered surfactants in their own right, because, as a general rule, glyceryl ethers and related compounds have insufficient solubility in water to act as effective surfactants. Thus, dodecylmonoglyceryl ether is relatively insoluble in water and has strongly lipophilic characteristics. None of the above-discussed references suggests that materials of the glyceryl ether type can have particular utility for grease and oil removal.

Concurrently filed U.S. application Ser. No. 644,214, P&G Attorney's Docket No. 2294, entitled DETERGENT COMPOSITIONS, by K. L. Jones, relates to a binary surfactant system consisting of an alkyl glyceryl ether in combination with certain nonionic surfactants, this system being a useful grease-removing ingredient in detergent compositions.

SUMMARY OF THE INVENTION

According to the invention, there are provided compounds of the general formula

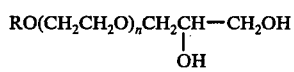

$$RO(CH_2CH_2O)_n CH_2CH(OH)-CH_2OH$$

wherein R is a straight chain or branched chain, substituted or unsubstituted, alkyl or alkenyl group of from about 8 to about 16 carbon atoms or an alkaryl group having an alkyl chain of from about 5 to about 14 carbon atoms and n is a number from 1 to about 6.

The above compounds are useful as surfactants, especially for grease and oil removal, and the invention also provides detergent compositions comprising a compound of the above formula as the sole surfactant or as one component of a surfactant system.

DETAILED DESCRIPTION OF THE INVENTION

The surfactant compounds of the present invention are based on a hydroxy-compound, ROH, wherein R is as defined above. Examples of suitable hydroxy-compounds include alkyl phenols and aliphatic alcohols.

Suitable alkyl phenols have an alkyl chain of from about 5 to about 13 carbon atoms and the alkyl substituent may be derived, for example, from polymerized propylene, diisobutylene, octene and nonene. Nonyl phenol is an especially useful example.

Examples of suitable aliphatic alcohols are tridecanol, myristyl alcohol and coconut fatty alcohol which is a mixture of fatty alcohols having alkyl chains of from 10–14 carbon atoms. Preferred alcohols are synthetic aliphatic alcohols made by the oxo process and marketed by the Shell Chemical Company under the trade name Neodol. These oxo alcohols are substantially straight chain primary alcohols having up to 25% $C_1$–$C_3$ alkyl branching at the 2-position. Secondary alcohols such as those marketed by the Union Carbide Corporation under the trade name Tergitol are also useful.

In preferred compounds of the invention, the group R is a substantially straight chain alkyl group having from about 10 to about 16 carbon atoms and there are from about 2 to about 5 moles of ethylene oxide per mole of surfactant compounds.

While not intending to be limited by theory, it is postulated that the surfactant compounds of the present invention derive their excellent grease and oil removal performance from the presence of a hydroxyl group on each of the terminal two carbon atoms of the hydrophilic chain. The linearity of this compact, hydrophilic head group and the relatively strong intermolecular hydrogen bonding afforded by the glyceryl group are believed to result in the formation of a highly dense monomolecular surfactant film at an oil/water interface. The resultant reduction in oil/water interfacial tension tends to encourage the removal of grease and oil stains from fabrics.

Simpler molecules having this type of structure, for example octadecane-1,2-diol, tend to have insufficient water-solubility to act as good detergents and the presence of the polyethoxylate moiety in the molecule aids water-solubility and enhances detergency.

To form the surfactant compounds of the present invention, the hydroxy-compound ROH wherein R is as defined above is ethoxylated with from 1 to about 6 moles of ethylene oxide per mole of hydroxy-compound and the ethoxylated material is then capped with a glyceryl moiety to form the monoglyceryl ether of the ethoxylated hydroxy-compound.

The relative degrees of hydrophobic and hydrophilic characters in the compounds of the present invention is therefore very important. In particular, longer-chain, more hydrophobic groups R would require more ethoxyl groups in the molecule to provide adequate solubility and this would make the hydrophilic group less compact.

Particularly preferred materials are 4, 7, 10, 13-tetraoxapentacosan-1, 2-diol and 4, 7, 10, 13, 16-penta-oxatriacontan-1, 2-diol.

The compounds of the present invention can be prepared in any suitable way.

For example, starting from the ethoxylated compound of the formula

    (I)

reaction with metallic sodium or sodium hydride yields the compound

    (II)

The above compound is then reacted with 3-chloro-1,2-propane diol, Cl—CH$_2$—CH(OH)—CH$_2$OH, to give the compound of the invention

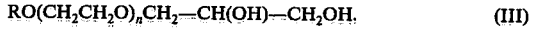    (III)

The compound can be purified by fractional distillation.

In an alternative synthesis, the ethoxylated compound (I) can be reacted under basic conditions with allyl chloride to form the allyl ether

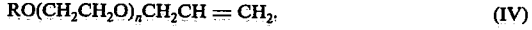    (IV)

Treatment of the allyl ether with a peracid, such as performic per peracetic acid, followed by hydrolysis yields the compound (III).

The compounds of the present invention are sufficiently water-soluble to be employed as the sole active organic detergent component in washing compositions. They may then be combined with inorganic or organic water-soluble or water-insoluble detergency builders, and with any other conventional components of detergent compositions.

The compounds may also be used in any ratio in combination with co-surfactants of the types discussed below. Preferably, the ratio of co-surfactant:glyceryl ether is in the range from about 10:1 to about 1:10, more preferably from about 4:1 to about 1:1. The total surfactant content of a detergent composition according to the invention is in the range from about 2% to about 95% by weight, typically from about 10% to about 20% in solid compositions and from about 30% to about 50% in liquid compositions. Low surfactant concentrations, for example 2 to 10%, are useful when the composition is designed for use without dilution. Compositions in the form of pastes or gels can have very high surfactant concentrations, up to 95%.

Co-Surfactants

Co-surfactants useful in detergent compositions of the present invention are selected from anionic, nonionic, zwitterionic and ampholytic surfactants.

Examples of the above types of co-surfactants are listed in U.S. Pat. No. 3,862,058 of Nirschl and Gloss, the disclosure of which is incorporated herein by reference.

Particularly useful anionic surfactants include alkyl sulfates and sulfonates containing from about 8 to about 18 carbon atoms; alkyl benzene sulfonates having from about 9 to about 20 carbon atoms in the alkyl chain, especially sodium or alkanolamine salts of linear straight chain alkyl benzene sulfonates in which the average chain length of the alkyl group is from about 10 to about 14, especially about 11·8 carbon atoms (normally abbreviated NaC$_{11.8}$LAS); alkyl ether sulfates of the formula

wherein R is alkyl or alkenyl of about 10 to about 20 carbon atoms, $n$ is 1 to 30 and M is an alkali metal cation; and olefin sulfonates derived by the sulfonation of C$_{12}$–C$_{24}$ α-olefins with sulfur trioxide.

Other useful anionic surfactants in combination with the surfactant compounds of the present invention are alkaline earth metal, preferably magnesium or calcium, salts of linear alkyl benzene sulfonic acid. The preferred material for this purpose is Mg(C$_{11.4}$LAS)$_2$.

Preferred nonionic surfactants include the condensation product of nonyl phenol with about 9.5 moles of ethylene oxide per mole of nonyl phenol, the condensation product of coconut fatty alcohol with about 6 moles of ethylene oxide per mole of coconut fatty alcohol, the condensation product of tallow fatty alcohol with about 9 moles of ethylene oxide per mole of tallow fatty alcohol and the condensation product of a secondary fatty alcohol containing about 15 carbon atoms with about 9 moles of ethylene oxide per mole of fatty alcohol.

Also useful are polyoxyethylene-polyoxypropylene condensates of the formula HO(C$_2$H$_4$O)$_n$(C$_3$H$_6$O)$_y$(C$_2$H$_4$O)$_z$H, where $y$ is at least 15 and the amount of (C$_2$H$_4$O)$_{x+z}$ equals from 20 to 90% of the total weight of the compound; alkyl polyoxypropylene-polyoxyethylene condensates of the formula RO(C$_3$H$_6$O)$_n$(C$_2$H$_4$O)$_y$H where R is a C$_1$–C$_{15}$ alkyl group and $n$ and $y$ are integers from 2 to 98.

Other useful nonionic surfactants are amine oxides, phosphine oxides and sulfoxides. Specific examples of such surfactants include dimethyldodecylamine oxide, dimethylstearylamine oxide, bis-(2-hydroxyethyl) dodecylamine oxide, dimethyldodecylphosphine oxide, dodecylmethyl sulfoxide and octadecyl methyl sulfoxide.

Ampholytic surfactants include derivatives of aliphatic or aliphatic derivatives of heterocyclic secondary and tertiary amines in which the aliphatic moiety can be straight chain or branches and wherein one of the aliphatic substituents contains from about 8 to 18 carbon atoms and at least one aliphatic substituent contains an anionic water-solubilizing group.

Preferred zwitterionic surfactants include higher alkyl or alkaryl ammonio propane sulfonates, such as 3-(N,N-dimethyl-N-hexadecylammonio) propane -1- sulfonate, 3-(N,N-dimethyl-N-hexadecylammonio)-2-hydroxy propane-1-sulfonate and 3-(N,N-dimethyl-N-alkylammonio-2-hydroxy propane-1-sulfonate, the alkyl group being derived from middle cut coconut fatty alcohol, and higher alkyl or alkaryl ammoniocarboxylates such as (N-dodecylbenzyl-N,N-dimethyl ammonio) acetate, (N,N-dimethyl-N-hexadecylammonio) acetate and 6-(N-dodecylbenzyl-N,N-dimethylammonio) hexansate. Other useful zwitterionic materials are the ethoxylated ammonio-sulfonates and sulfates disclosed in U.S. patent application Ser. No. 493,953, filed Aug. 1, 1974.

Builder Salts

Detergent compositions of the present invention preferably include builder salts, especially alkaline, polyvalent anionic builder salts. These alkaline salts serve to maintain the pH of the laundry solution in the range from about 7 to about 12, preferably from about 8 to about 11.

Suitable detergent builder salts useful herein can be of the poly-valent inorganic or poly-valent organic types, or mixtures thereof. Non-limiting examples of suitable water-soluble, inorganic alkaline detergent builder salts include the alkali metal carbonates, borates, phosphates, polyphosphates, bicarbonates, silicates and sulfates. Specific examples of such salts include the sodium and potassium tetraborates, perborates, bicarbonates, carbonates, tripolyphosphates, orthophosphates and hexametaphosphates.

Examples of suitable organic alkaline detergency builder salts are: (1) water-soluble amino polyacetates, e.g., sodium and potassium ethylenediamine tetraacetates, nitrilotriacetates and N-(2-hydroxyethyl) nitrilodiacetates; (2) water-soluble salts of phytic acid, e.g., sodium and potassium phytates; (3) water-soluble polyphosphonates, including, sodium, potassium and lithium salts of ethane-1-hydroxy-1,1-diphosphonic acid; sodium, potassium and lithium salts of methylenediphosphonic acid and the like.

Additional organic builder salts useful herein include the polycarboxylate materials described in U.S. Pat. No. 2,264,103, including the water-soluble alkali metal salts of mellitic acid. The water-soluble salts of polycarboxylate polymers and copolymers such as are described in U.S. Pat. No. 3,308,067, incorporated herein by reference, are also suitable herein. It is to be understood that while the alkali metal salts of the foregoing inorganic and organic poly-valent anionic builder salts are preferred for use herein from an economic standpoint, the ammonium, alkanolammonium, e.g., triethanolammonium, diethanolammonium, and the like, water-soluble salts of any of the foregoing builder anions are useful herein.

Mixtures of organic and/or inorganic builders can be used herein. One such mixture of builders is disclosed in Canadian Pat. No. 755,038, e.g., a ternary mixture of sodium tripolyphosphate, trisodium nitrilotriacetate and trisodium ethane-1-hydroxy-1,1-diphosphonate.

While any of the foregoing alkaline poly-valent builder materials are useful herein, sodium tripolyphosphate, sodium nitrilotriacetate, sodium mellitate, sodium citrate and sodium carbonate are preferred herein for this builder use. Sodium tripolyphosphate is especially preferred herein as a builder both by virtue of its detergency builder activity and its ability to suspend illite and kaolinite clay soils and retarding their redeposition on the fabric surface.

Another type of detergency builder material useful in the present compositions comprises a water-soluble material capable of forming a water-insoluble reaction product with water hardness cations in combination with a crystallization seed which is capable of providing growth sites for said reaction product. Such "seeded builder" compositions are fully disclosed in Belgian Pat. No. 798,856, issued Oct. 29, 1973, the disclosure of which is incorporated herein by reference.

Specific examples of materials capable of forming the water-insoluble reaction product include the water-soluble salts of carbonates, bicarbonates, sesquicarbonates, silicates, aluminates, and oxalates. The alkali metal, especially sodium, salts of the foregoing materials are preferred for convenience and economy.

Another type of builder useful herein includes various substantially water-insoluble materials which are capable of reducing the hardness content of laundering liquors, e.g., by ion-exchange processes. Examples of such builder materials include the phosphorylated cloths disclosed in U.S. Pat. No. 3,424,545, inventor Benjamin, issued Jan. 28, 1969, incorporated herein by reference.

The complex aluminosilicates, i.e., zeolite-type materials, are useful presoaking/washing adjuvants herein in that these materials soften water, i.e., remove $Ca^{++}$ hardness. Both the naturally occurring and synthetic "zeolites", especially zeolite A and hydrated zeolite A materials, are useful for this builder/softener purpose. A description of zeolite materials and a method of preparation appears in Milton, U.S. Pat. No. 2,882,243, issued Apr. 14, 1959, incorporated herein by reference. The copending application of Corkill et al, entitled DETERGENT COMPOSITION, Ser. No. 450,266, filed Mar. 11, 1974, describes the use of hydrated synthetic zeolites as builders and is also incorporated herein by reference.

The detergent builders are used at concentrations of from about 10 to about 60%, preferably 20 to 50%, by weight of the detergent compositions of this invention.

Other Components

In addition to the above-described surfactant or builder components, the present compositions can optionally contain a wide variety of other conventional detergency adjuncts. Representative materials of this type include, for example, the various anticaking agents, filler materials, soil suspending agents such as carboxymethylcellulose, optical brighteners, anti-spotting agents, dyes, perfumes, suds boosters, suds depressants, and the like. These adjunct materials are commonly used as minor components (e.g., 0.1 to 5% wt.) in compositions of the present type.

Highly preferred optional additives herein include various bleaches commonly employed in presoak, laundry additive and detergent compositions. Such bleaches can include, for example, the various organic peroxyacids such as peradipic acid, perphthalic acid, diperphthalic acid, diperazelaic acid and the like. Inorganic bleaches, i.e. persalts including such materials as sodium perborate, sodium perborate tetrahydrate, urea peroxide, and the like, can be employed in the compositions herein. Bleaches are commonly used in the instant granular compositions at a level of from about 1 to about 45% by weight.

An especially preferred bleaching agent for use herein is sodium perborate tetrahydrate, at an effective concentration of from about 10 to about 30% by weight of the total composition.

Liquid or pasty compositions, in particular, can include materials to impart alkalinity to the detergent solution; typical of such materials are mono-, di- and tri-ethanolamine.

Various detergency enzymes well known in the art for their ability to degrade and aid in the removal of various soils and stains can also be employed in the present granular compositions. Detergency enzymes are commonly used at concentrations of from about 0.1 to about 1.0% by weight of such compositions. Typical enzymes include the various proteases, lipases, amylases, and mixtures thereof, which are designed to remove a variety of soils and stains from fabrics.

Composition Preparation

Compositions of the present invention can be prepared in any of a wide variety of product forms, for example as granules, powder, liquid, gel, paste or tablets. Where a solid product form is desired, a granular composition is generally preferred and a slurry comprising a builder salt such as sodium tripolyphosphate and the surfactant system can be spray-dried to form granules. Alternatively, the product may be agglomerated, and this is preferred with certain nonionic surfactants which are relatively low-boiling and may degrade during spray drying.

In especially preferred compositions, the product is prepared in liquid form. Liquid products are very useful for grease removal as they can safely be used without dilution as a pre-treatment for oily stains. In liquid formulations, the surfactant mixture is normally dissolved in water or a wateralcohol mixture, preferred alcohols being $C_1$-$C_3$ alkanols, especially ethanol. In liquid formulations, particularly preferred co-surfactants are the magnesium, calcium, triethanolammonium and monoethanolammonium salts of LAS.

The following examples illustrate the present invention.

EXAMPLE I

Preparation of 4, 7, 10, 13-tetraoxatricosan-1, 2-diol
Sodium salt of 3, 6, 9-trioxanoadecan-1-ol ($C_{10}E_3$)

Sodium hydride (7.4 g.) was mixed with anhydrous diethyl ether (200 ml.) and $C_{10}E_3$ (88.5 g.) was added dropwise under nitrogen over a period of 1 hour 20 minutes. The reaction continued for a further hour, after which time the sodium salt of $C_{10}E_3$ had been formed.

Glyceryl ether of $C_{10}E_3$

To the above reaction mixture at room temperature was added dropwise 3-chloro-1, 2-propane diol (33.7 g.) which resulted in a slight temperature rise and loss of diethyl ether. The reaction product was a creamy yellow slurry. The slurry was centrifuged for seven minutes at 1300 r.p.m. and solid sodium chloride was thereby separated to yield a viscous liquid. The liquid was subsequently extracted into ether over saturated sodium chloride solution. Evaporation of the ether extract and filtration under suction of the product (which contained some sodium chloride) yielded the glyceryl ether of $C_{10}E_3$ as a colorless liquid. The filtrate was tested with silver nitrate and was shown to contain no chloride ion. The presence of the title compound was confirmed by IR and NMR spectra.

EXAMPLE II

Preparation of 4, 7, 10, 13-tetraoxapentacosan-1, 2-diol
Allyl ether of 3, 6, 9-trioxa-eicosan-1-ol ($C_{12}E_3$)

Sodium hydride (2.7 g; 80% dispersion in mineral oil) was treated, under nitrogen, with $C_{12}E_3$ (24.8 g) in dry tetrahydrofuran (80 ml) and the temperature was raised to 55°. After one hour, allyl chloride (6.4 g) in tetrahydrofuran (40 ml) was added dropwise. The mixture was then boiled under reflux for 16 hours by which time precipitated sodium chloride was visible in the reaction medium. After cooling the reaction to room temperature, water (250 ml) was added and the upper, organic phase was separated, dissolved in ether and washed with water. Drying of the ether solution followed by evaporation of ether left a residue of the allyl ether [23 g; 96% by gas-liquid chromatography (GLC). The infra-red spectrum showed the absence of absorption due to hydroxy groups and absorption at 1640, 995 and 923 cm$^{-1}$ (—CH = CH$_2$).

Glyceryl ether of $C_{12}E_3$

The allyl ether (5.7 g) in formic acid (40 ml; 98%) was treated with hydrogen peroxide (4 ml; 30% w/v) which was added in four equal portions during 30 minutes. The reaction temperature was raised to 60° and after 48 hours no hydrogen peroxide could be detected. Sodium sulphite (0.2 g) was added and then formic acid and water were removed at water pump vacuum. The residue was hydrolysed in ethanol (40 ml) containing aqueous potassium hydroxide (2 M; 40 ml) for 1 hour at 75°–80°. Extraction of the cooled hydrolysate with ether yielded a product (5.2 g) containing 70% of the glyceryl ether of $C_{12}E_3$ (by GLC). Fractional distillation gave purified (97% pure) glyceryl ether, b.p. 206°–210°/0.7 mm. Found: C, 64.0; H, 11.1%, $C_{21}H_{44}O_6$ requires: C, 64.3; H, 11.2%.

EXAMPLE III

Detergent compositions were prepared by combining 0.4 g of a nonionic surfactant with 0.7 g of sodium perborate and 2.6 g of a carrier granule which consists of sodium tripolyphosphate (57%), sodium sulphate (19%), silicate solids (10%) linear alkyl benzene sulphonate (1.5%), minor ingredients (1.5%) and water (11%).

Compositions were prepared using, as nonionic surfactant (a) the glyceryl ether of $C_{12}E_3$, (b) the glyceryl ether of $C_{14}E_4$; and (c) as control, a $C_{14}$–$C_{15}$ aliphatic alcohol condensed with an average 7 moles of ethylene oxide.

Performance Data

Compositions (a), (b) and (c) above were tested in the following manner:

Pre-washed polyester-cotton cloths were stained with (1) dirty motor oil, (2) natural body soil, (3) lipstick and (4) eye shadow. The cloths were split into halves for interproduct comparison.

The cloths were washed in a simulated washing machine for 15 minutes at 50° C using compositions (a), (b) and (c) in 500 ml of water of 12° hardness. The half-cloths were compared for stain removal by a panel of judges using a 0-4 judgment scale. The following results were obtained.

|  | Assessment in panel score units | |
|---|---|---|
|  | Compositions | |
| Stain | (c) | (a) |
| Dirty motor oil | −0.86 | +1.02* |
| Lipstick | +0.66 | −0.08 |
| Eye shadow | −1.05 | +0.58* |
| Body soil | +0.05 | −0.44 |
|  | (c) | (b) |
| Dirty motor oil | −0.63 | +0.16* |
| Body soil | −0.05 | −0.38 |
| Eye shadow | −1.05 | −0.47* |

*represents a significant difference at the 95% confidence level

As can be seen from the above results, the compositions of the present invention can offer a significant improvement in oily stain removal.

EXAMPLE IV

Useful liquid detergent compositions of the invention which provide effective oil stain removal in a laundering process are exemplified by the following compositions.

| Ingredient | Composition (wt. %) | | | |
|---|---|---|---|---|
|  | (a) | (b) | (c) | (d) |
| Glyceryl ether of $C_{12}E_3$ | 30 | 15 | 20 | 10 |
| Monoethanolammonium $C_{11.4}$ LAS | 18 |  |  | 20 |
| Mg $(C_{11.4}$ LAS$)_2$ |  | 30 |  |  |
| Condensation product of 6 moles of ethylene oxide with 1 mole of coconut fatty alcohol |  |  | 20 |  |
| Sodium nitrilotriacetate |  |  |  | 12 |
| Monoethanolamine | 2 | 3 |  |  |
| Oleic acid | 1 | 2 |  |  |
| Ethanol | 5 | 5 | 10 | 14 |
| Water and minors | to 100 | to 100 | to 100 | to 100 |

EXAMPLE V

Useful granular detergent compositions of the present invention are exemplified as follows.

| Ingredient | Composition (wt. %) | | |
|---|---|---|---|
|  | (a) | (b) | (c) |
| Glyceryl ether of $C_{12}E_3$ | 18 | 10 | 8 |
| Dobanol 91-8* |  | 10 |  |
| 3-(N,N-dimethyl-N-hexadecylammonio) propane-1-sulfonate |  |  | 16 |
| Sodium carbonate | 10 | 12 | 10 |
| Sodium silicate ($SiO_2$:$Na_2O$ = 1.6) | 10 | 10 | 14 |
| Sodium tripolyphosphate | 25 | 30 | 35 |
| Sodium sulphate | 28 | 20 | 10 |
| Moisture and minors | to 100 | to 100 | to 100 |

*A condensate of 8 moles of ethylene oxide with 1 mole of a $C_9$-$C_{11}$ aliphatic alcohol marketed by Shell Chemical Co.

What is claimed is:

1. A detergent composition, having a pH of from about 8 to about 11 when used in the laundry solution, consisting essentially of:
   (a) from 2% to about 95% of a compound of the formula

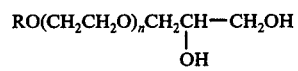

wherein R is an alkyl or alkenyl group of from about 8 to about 18 carbon atoms or an alkaryl group having from about 5 to about 14 carbon atoms in the alkyl chain, and n is from about 2 to about 5;
   (b) from 0 to about 98% of detergency builders;
   (c) from 0 to about 98% of anticaking agents;
   (d) from 0 to about 98% of filler materials;
   (e) from 0 to about 98% of soil suspending agents;
   (f) from 0 to about 98% of optical brighteners;
   (g) from 0 to about 98% of antispotting agents;
   (h) from 0 to about 98% of dyes;
   (i) from 0 to about 98% of perfumes;
   (j) from 0 to about 98% of suds boosters;
   (k) from 0 to about 98% of suds depressants;
   (l) from 0 to about 98% of bleaching agents;
   (m) from 0 to about 98% of alkalinity sources;
   (n) from 0 to about 98% of enzymes;
   (o) from 0 to about 98% water; and
   (p) from 0 to about 98% of $C_1$-$C_3$ alkanols.

2. A composition according to claim 1 comprising from about 10 to about 50% of said compound and from about 10 to about 60% of a detergency builder.

3. A detergent composition consisting essentially of:
   (a) from 2 to about 95% of a mixture consisting essentially of:
      (1) a compound of the formula

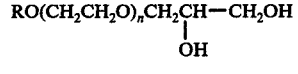

wherein R is a $C_8$-$C_{16}$ alkyl or alkenyl group or an alkaryl group having from 5 to 13 carbon atoms in the alkyl chain, and *n* is from about 2 to about 5; and
      (2) a co-surfactant selected from the group consisting of anionic, nonionic, zwitterionic and ampholytic surfactants;
      the ratio of (1) to (2) being from 10:1 to 1:10;
   (b) from 0 to about 98% of detergency builders;
   (c) from 0 to about 98% of anticaking agents;
   (d) from 0 to about 98% of filler materials;
   (e) from 0 to about 98% of soil suspending agents;
   (f) from 0 to about 98% of optical brighteners;
   (g) from 0 to about 98% of antispotting agents;
   (h) from 0 to about 98% of dyes;
   (i) from 0 to about 98% of perfumes;
   (j) from 0 to about 98% of suds boosters;
   (k) from 0 to about 98% of suds depressants;

(l) from 0 to about 98% of bleaching agents;
(m) from 0 to about 98% of alkalinity sources;
(n) from 0 to about 98% of enzymes;
(o) from 0 to about 98% water; and
(p) from 0 to about 98% of $C_1$–$C_3$ alkanols.

4. A composition according to claim 3 wherein R is an alkyl group having 10 to 14 carbon atoms.

5. A composition according to claim 3 wherein the ratio of (a) to (b) is from 1:1 to 1:4.

6. A composition according to claim 3 wherein the co-surfactant is an anionic surfactant selected from alkali metal, calcium, magnesium, ammonium and alkanolammonium ($C_9$–$C_{20}$ alkyl) benzene sulfonates, $C_8$–$C_{18}$ alkyl sulfates, $C_8$–$C_{18}$ alkyl sulfonates, ($C_{10}$–$C_{20}$ alkyl) ether sulfates containing an average of 1 to 30 ethylene oxide groups, and olefin sulfonates derived from $C_{12}$–$C_{24}$ α-olefins.

7. A composition according to claim 3, additionally comprising from about 10 to about 60% of a detergency builder.

8. A composition according to claim 3 comprising from about 10 to about 50% of said mixture and from about 10 to about 60% of a detergency builder.

* * * * *